United States Patent [19]

Kress et al.

[11] Patent Number: 4,657,955
[45] Date of Patent: Apr. 14, 1987

[54] FLAMEPROOFING AGENTS, THEIR PREPARATION AND THEIR USE FOR FLAMEPROOFING POLYCARBONATES

[75] Inventors: Hans-Jürgen Kress, Krefeld; Klaus Kircher, Leverkusen, both of Fed. Rep. of Germany

[73] Assignee: Bayer Aktiengesellschaft, Leverkusen, Fed. Rep. of Germany

[21] Appl. No.: 872,791

[22] Filed: Jun. 11, 1986

Related U.S. Application Data

[62] Division of Ser. No. 654,582, Sep. 26, 1984, Pat. No. 4,615,832.

[30] Foreign Application Priority Data

Sep. 26, 1983 [DE] Fed. Rep. of Germany ....... 3334822

[51] Int. Cl.⁴ .............................................. C08K 5/34
[52] U.S. Cl. ...................... 524/94; 524/130; 524/156; 524/161; 524/165; 524/166
[58] Field of Search ................ 524/94, 130, 156, 161, 524/165, 166

[56] References Cited

U.S. PATENT DOCUMENTS

| | | | |
|---|---|---|---|
| 2,876,251 | 3/1959 | Barnhart et al. | 260/471 |
| 3,775,367 | 11/1973 | Nouvertne | 260/45.9 R |
| 3,836,490 | 9/1974 | Bockmann et al. | 524/288 |
| 3,873,587 | 3/1975 | Rosenthal et al. | 260/429.5 |
| 3,919,167 | 11/1975 | Mark | 524/94 |
| 3,940,366 | 2/1976 | Mark | 524/163 |
| 3,948,851 | 4/1976 | Mark | 524/163 |
| 3,953,397 | 4/1976 | Richter et al. | 524/94 |
| 4,039,509 | 8/1977 | Mark | 524/94 |
| 4,093,590 | 6/1978 | Mark | 524/162 |
| 4,115,354 | 9/1978 | Mark et al. | 524/162 |
| 4,208,489 | 6/1980 | Schmidt et al. | 525/146 |
| 4,552,911 | 11/1985 | Cohnen et al. | 524/94 |

FOREIGN PATENT DOCUMENTS 2703710 8/1978 Fed. Rep. of Germany .
3203905 8/1983 Fed. Rep. of Germany ........ 524/94

Primary Examiner—John Kight
Assistant Examiner—Kriellion Morgan
Attorney, Agent, or Firm—Gene Harsh; Joseph C. Gil; Aron Preis

[57] ABSTRACT

The present invention relates to new phthalimides of the formula (I)

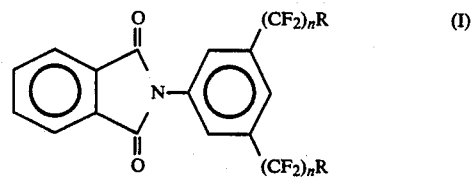

wherein
n is an integer of from 1 to 12, preferably 1 to 4 and especially 1 to 2 and
R is H or F, and their preparation, these phthalimides being suitable, in combination with alkali metal salts, as flameproofing agent combinations for thermoplastic, branched, aromatic polycarbonates.

3 Claims, No Drawings

FLAMEPROOFING AGENTS, THEIR PREPARATION AND THEIR USE FOR FLAMEPROOFING POLYCARBONATES

This application is a division of application Ser. No. 654,582 filed Sept. 26, 1984 now U.S. Pat. No. 4,615,832.

The present invention relates to phthalimide compounds of the formula (I)

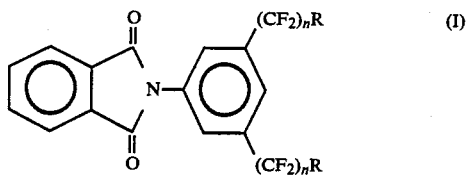

wherein
n is an integer from 1 to 12, preferably 1 to 4 especially 1 to 2 and
R is H or F.

The present invention also relates to the preparation of phthalimides of the formula (I), which is characterized in that phthalic anhydride is reacted with an amine of the formula (II)

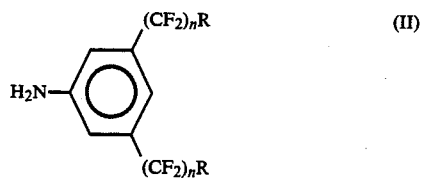

wherein
n is an integer from 1 to 12, preferably 1 to 4 and especially 1 to 2 and
R is H or F in equimolar amounts at about 117° C., also using glacial acetic acid as a solvent and cyclohexane as a waterentraining agent.

The amines of the formula (II) are known from the literature, or they can be obtained by processes which are known from the literature, such as those described, for example, for 3,5-bistrifluoromethylaniline by Maginnity et al., J. Am. Soc. 73 (1951) page 3579 or Ross et al., J. Am. Soc. 75 (1953) page 4967, and for 3,5-bis-tetrafluoroethylaniline in U.S. Pat. No. 2,876,251.

The amount of solvent to be employed is about 2.5 liters of glacial acetic acid per mol of the aniline according to the invention; the corresponding amount of water-entraining agent is about 300 ml.

In combination with the known flameproofing agents for polycarbonates, that is to say the alkali metal salts of organic or inorganic acids, the new phthalimide compounds are suitable synergistic agents for improving the flame-repellancy of thermoplastic, branched, aromatic polycarbonates prepared only from halogen-free phenolic components.

The present invention thus also relates to flameproofing agent combinations consisting of (a) 0.1 to 1 part by weight of a phthalimide of the formula (I) and (b) 0.02 to 2 parts by weight of an alkali metal salt of an organic or inorganic acid, in particular a sodium, potassium or lithium salt.

Alkali metal salts of organic or inorganic acids which are suitable flameproofing agents are mentioned, for example, in German Offenlegungsschriften No. 2,703,710, No. 2,918,882 and No. 2,918,883.

The present invention furthermore relates to the use of the flameproofing agent combinations according to the invention for flameproofing thermoplastic, branched, aromatic polycarbonates of halogen-free phenolic components in amounts of 0.1 to 1% by weight, based on the thermoplastic, branched, aromatic polycarbonate, of phthalimide of the formula (I) and 0.02 to 2% by weight, based on the thermoplastic, branched, aromatic polycarbonate, of alkali metal salt of an organic or inorganic acid.

The present invention moreover relates to a process for flameproofing thermoplastic, branched, aromatic polycarbonates of halogen-free phenolic components, which is characterised in that the flameproofing agent combinations according to the invention are incorporated, individually as single components or as a mixture, by mixing and subsequent granulation via a twin-screw extruder at a composition temperature of 280°-310° C., preferably 290°-300° C.

The optimum processing conditions are such that a throughput of 5 kg/hour is achieved at a speed of rotation of 80–100 revolutions/minute.

The unit used is an extruder from Werner and Pfleiderer with the designation ZSK 32.

The present invention furthermore relates to thermoplastic moulding compositions based on aromatic, branched, thermoplastic polycarbonates of halogen-free phenolic components containing 0.1 to 1% by weight of phthalimide of the formula (I) and 0.02 to 2% by weight of alkali metal salt of an inorganic or organic acid, the two ranges for the percentages by weight in each case being based on the thermoplastic, branched, aromatic polycarbonate, without other additives.

Aromatic, branched, thermoplastic polycarbonates of halogen-free phenolic components are to be understood as meaning that the diphenols, monophenols and trisphenols, tetraphenols or other branching agents to be employed for the preparation of the polycabonates have no halogen substituents. These polycarbonates, for example if they are prepared by the phase boundary process using phosgene, can of course still contain small residual ppm amounts of non-hydrolysed chlorine. In the subsequent characterisation of the polycarbonates as "halogen-free", radicals of saponifiable halogen of this type should not be taken into consideration.

Chlorine-free and bromine-free flameproofed polycarbonates with a UL 94 V classification are thus possible with the aid of these new flameproofing agents. In addition, the phthalimides of the formula (I) according to the invention are characterised by a low volatility under normal polycarbonate processing conditions.

The polycarbonate moulding compositions according to the invention achieve a classification in burning class V0 in accordance with Underwriters' Laboratories Inc., Bulletin 94, Combustion Tests for the Classification of Materials (called UL 94 below), on test pieces with dimensions 127×12.7×3.2 mm (⅛") or 127×12.7×1.6 mm (1/16"), that is to say they do not drip and have an average after-burn time of ≦5 seconds.

Test pieces with the dimensions 127×12.7×0.8 mm (1/32") achieve a classification in burning class V 1, that is to say they do not drip and have an average after-burn time of ≦25 seconds.

It is known that the flameproof characteristics of polycarbonates can be improved by additions of alkali metal salts, it being possible for the polycarbonates to be either halogen-free or substituted by halogen.

(See, for example, German Offenlegungsschrift No. 1,930,257, German Offenlegungsschrift No. 2,049,358, German Offenlegungsschrift No. 2,112,987, German Offenlegungsschrift No. 2,149,311, German Offenlegungsschrift No. 2,253,072, German Offenlegungsschrift No. 2,458,968, German Offenlegungsschrift No. 2,461,063, German Offenlegungsschrift No. 2,461,146 and German Offenlegungsschrift No. 2,461,077).

It is known that the flameproof characteristics of polycarbonates can be improved by mixtures of organic chlorine compounds and certain inorganic salts (see, for example, German Offenlegungsschrift No. 2,013,496; tetrachlorophthalic anhydride, inter alia, is mentioned as a suitable organic chlorine compound).

It is known that polycarbonates can be rendered flame-repellant with brominated phthalimides (see U.S. Pat. No. 3,873,587).

It is also known that phthalimide compounds can be used in combination with alkali metal salt additives, exclusively halogenated phthalimides being used (German Offenlegungsschriften Nos. 2,707,928, 2,740,850 and 2,703,710).

It is also known that organic halogen compounds, such as halogenated phthalimides, can be used in combination with alkali metal salts and substances which reduce the tendency of polycarbonates to drip for flameproofing polymer alloys based on polycarbonates (see German Offenlegungsschrift No. 2,918,882 and German Offenlegungsschrift No. 2,918,883).

It is also known that moulding compositions of branched aromatic polycarbonates together with alkali metal salts and halogenated phthalimides and an additional bromine content can be rendered flame-repellant for extreme flaming conditions (see German Offenlegungsschrift No. 3,203,905).

In our opinion, however, neither the phthalimides of the formula (I) nor their use as a flameproofing synergist for halogen-free polycarbonates are anticipated or suggested in the literature references mentioned.

There is also as yet no additive combination known which, after admixing of such small amounts by weight of a chlorine- and bromine-free phthalimide already give polycarbonate moulding compositions of burning classes V 0 according to UL 94 at a wall thickness of ⅛" and 1/16" and of V 1 at a wall thickness of 1/32".

The admixing, claimed according to the invention, of phthalimides of the general formula (I) is thus particularly advantageous, because compounds of these classes of substance are stable to heat, have a low volatility, are stable to hydrolysis and can readily be mixed into polycarbonate.

Examples of suitable alkali metal salts of inorganic acids in the context of the invention are those of inorganic proton acids. In the context of the invention, inorganic proton acids are Brönsted acids which can form alkali metal salts (for the expression "Brönsted acid", compare Fieser & Fieser "Organic Chemistry", 1965, page 595, Interscience Publishers N.Y., USA), such as, for example, meta-, ortho- or pyro-phosphoric acid and proton acids of complex fuorine/metal compounds.

Suitable alkali metal salts of organic acids in the context of the invention are those of organic Brönsted acids with at least one carbon atom which can form alkali metal salts. Such optionally substituted organic acids can be OH or NH acid compounds, such as, for example, sulphonic acids, phosphonic acids, thiophosphonic acids, NH-acid sulphonamides or sulphonimides. They must have at least one C atom and can preferably contain between 2 and 30 C atoms.

The alkali metal salts which are suitable according to the invention should preferably have a pH value of between 5 and 9, in particular between 6.5 and 7.5, measured on 1% strength by weight solutions or suspensions of the salts in water at 20° C.

Preferred alkali metal salts are the potassium, sodium and lithium salts, especially the potassium salts.

Preferred alkali metal salts of organic acids are the sodium, potassium and lithium salts, but especially the potassium salts of organic sulphonic acids and phosphonic acids, the organic radicals of which can optionally be substituted by halogens, such as fluorine, chlorine or bromine. Examples which may be mentioned are: sodium perfluorobutanesulfate or potassium perfluorobutanesulphate, sodium perfluoromethanesulphonate or potassium perfluoromethanesulphonate, sodium 2,5-dichlorobenzenesulphonate or potassium 2,5-dichlorobenzenesulphonate, sodium 2,4,5-trichlorobenzenesulphonate or potassium 2,4,5-trichlorobenzenesulphonate, sodium (4-chlorophenyl)-phosphonate or potassium (4-chlorophenyl)-phosphonate, sodium methylphosphonate or potassium methylphosphonate, sodium (2-phenylethylene)-phosphonate or potassium (2-phenylethylene)-phosphonate, and lithium phenylphosphonate.

Preferred alkali metal salts of inorganic acids are the sodium, potassium and lithium salts, but especially the potassium salts of proton acid/fluorine/metal complex compounds and of meta-, ortho- or pyro-phosphoric acid.

Examples which may be mentioned are: trisodium or tripotassium hexafluoroaluminate, disodium or dipotassium hexafluorotitanate, disodium or dipotassium hexafluorosilicate, disodium or dipotassium hexafluorozirconate, sodium pyrophosphate or potassium pyrophosphate, sodium metaphosphate or potassium metaphosphate, sodium tetrafluoborate or potassium tetrafluoborate, sodium hexafluorophosphate or potassium hexafluorophosphate and sodium phosphate, potassium phosphate or lithium phosphate.

Particularly suitable salts are: potassium perfluorobutanesulphonate or sodium perfluorobutanesulphonate, potassium 2,5-dichlorobenzenesulphonate or sodium 2,5-dichlorobenzenesulphonate, potassium 2,4,5-trichlorobenzenesulphonate or sodium 2,4,5-trichlorobenzenesulphonate, potassium hexafluoroaluminate, potassium pyrophosphate, potassium methylphosphonate, sodium hexafluoroaluminate and lithium phenylphosphonate.

Mixtures of the salts with one another are also suitable.

Halogen-free aromatic, branched, thermoplastic polycarbonates in the context of the present invention are polycondensates which are obtainable by reaction of halogen-free diphenols, in particular dihydroxydiarylalkanes, with phosgene or diesters of carbonic acid, dihydroxydiarylalkanes in which the aryl radicals carry alkyl groups in the o-position and/or m-position relative to the hydroxyl group also being suitable, in addition to unsubstituted dihydroxydiarylalkanes, these polycondensates being branched by incorporation of amounts of between 0.05 and 2.0 mol % (based on the diphenols used) of compounds which are trifunctional or more than trifunctional, for example those with three or more than three phenolic hydroxyl groups.

Polycarbonates of this type and their preparation are described, for example, in German Offenlegungsschriften Nos. 1,570,533, 1,595,762, 2,116,974 and 2,113,347, British Patent Specification No. 1,079,821, U.S. Pat. No. 3,544,514 and German Offenlegungsschrift No. 2,500,092.

The halogen-free aromatic, branched, thermoplastic polycarbonates have average weight-average molecular weights $\overline{M}w$ of between 15,000 and 100,000, preferably between 20,000 and 80,000, determined by measurement of the relative viscosity in $CH_2Cl_2$ at 25° C. at a concentration of 0.5 g/100 ml, after appropriate calibration.

Examples of suitable halogen-free diphenols are hydroquinone, resorcinol, 4,4'-dihydroxydiphenyl, bis-(hydroxyphenyl)-alkanes, such as, for example, $C_1$–$C_8$-alkylene- or $C_2$–$C_8$-alkylidene-bisphenols, bis-(hydroxyphenyl)-cycloalkanes, such as, for example, $C_5$–$C_{15}$-cycloalkylene- or $C_5$–$C_{15}$-cycloalkylidene-bisphenols, bis-(hydroxyphenyl) sulphides, ethers, ketones, sulphoxides or sulphones, and furthermore α,α'-bis-(hydroxyphenyl)-diisopropylbenzene and the corresponding nuclear-alkylated compounds. Polycarbonates based on 2,2-bis-(4-hydroxyphenyl)-propane (bisphenol A), 2,2-bis-(4-hydroxy-3,5-dimethylphenyl)-propane (tetramethylbisphenol A), 1,1-bis-(4-hydroxyphenyl)-cyclohexane (bisphenol Z) and trinuclear bisphenols, such as α,α'-bis-(4-hydroxyphenyl)-p-diisopropylbenzene, are preferred.

Other halogen-free diphenols which are suitable for the preparation of the polycarbonates are described in U.S. Pat. Nos. 3,028,365 and 3,275,601.

Examples of some of the compounds which can be used and have three or more than three phenolic hydroxyl groups are phloroglucinol, 4,6-dimethyl-2,4,6-tri-(4-hydroxyphenyl)-hept-2-ene, 4,6-dimethyl-2,4,6-tri-(4-hydroxyphenyl)-heptane, 1,3,5-tri-(4-hydroxyphenyl)-benzene, 1,1,1-tri-(4-hydroxyphenyl)-ethane, tri-(4-hydroxyphenyl)-phenylmethane, 2,2-bis-[4,4-bis-(4-hydroxyphenyl)-cyclohexyl]-propane, 2,4-bis-(4-hydroxyphenyl-isopropyl)-phenol, 2,6-bis-(2'-hydroxy-5'-methylbenzyl)-4-methylphenol, 2-(4-hydroxyphenyl)-2-(2,4-dihyroxyphenyl)-propane, hexyl (4-(4-hydroxyphenyl-isopropyl)-phenyl)-orthoterephthalate, tetra-(4-hydroxyphenyl)-methane, tetra-(4-(4-hydroxyphenylisopropyl)-phenoxy)-methane and 1,4-bis-((4',4''-dihydroxytriphenyl)-methyl)-benzene. Some of the other trifunctional compounds are 2,4-dihydroxybenzoic acid, trimesic acid, cyanuric chloride, 3,3-bis-(4-hydroxyphenyl)-2-oxo-2,3-dihydroindole and 3,3-bis-(4-hydroxy-3-methylphenyl)-2-oxo-2,3-dihyroindole.

Examples of suitable chain stoppers for regulating the molecular weight are, in a known manner, phenol and alkylphenols, which can be used in the known amounts.

The aromatic, branched, thermoplastic polycarbonates are prepared in a known manner, for example by the phase boundary process or by the process in homogeneous solution. The aromatic, thermoplastic polycarbonates can also be prepared by the known transesterification process.

Particularly preferred polycarbonates in the context of the present invention are branched polycarbonates based on bisphenol A with a branching agent content of 0.3 to 1.0 mol %, based on the mol of bisphenol A.

Examples of suitable amines of the formula II are

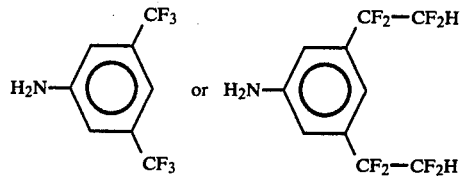

These are described in Maginnity et al., J. Am. Soc. 73 (1951) page 3579 and in U.S. Pat. No. 2,876,251.

Examples of suitable phthalimide compounds of the formula I are

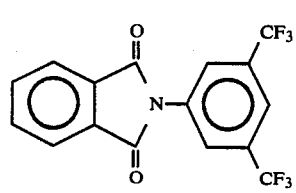

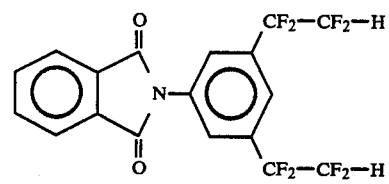

These can be prepared by the process of the example and under the abovementioned general process conditions.

The flameproofing agent combinations according to the invention can be prepared before hand by mixing the individual components or as a concentrate in the polycarbonate, and can, for example, be stored before being used.

The new flameproofing agent combination can be incorporated into the polycarbonates individually in the form of its components or as a mixture, for example by mixing and subsequent granulation of the material via a twin-screw extruder at 280° to 310° C.

The moulding compositions, according to the invention, based on polycarbonate and flameproofing agent combination can also contain other additives customary in polycarbonate chemistry, such as, for example, pigments, dyestuffs, fillers, stabilisers or mould release agents.

The moulding compositions according to the invention can be processed to shaped articles or films.

Shaped articles are produced by the injection-moulding process at a temperature of 300°–310° C.

The moulding compositions according to the invention can be used, for example, in the electrical field for switch shields, sockets, socket plates, switch boxes and the like, in the household sector for housing components for irons and coffee machines, and in the field of large-scale equipment, for example for computer housing components.

Description of the combustion test

Polycarbonate samples are shaped to bars having the dimensions 127×12.7×0.8 (or 1.6 or 3.2) mm (5.00×0.5×1/32 (or 1/16 or ⅛) inches in accordance with the UL 94 test (Underwriters' Laboratories, Inc.). The bars are mounted vertically such that the bottom surface of the test piece is 305 mm above a strip of bandaging material. Each test bar is ignited individually by means of two successive ignition operations lasting 10 seconds, and the burning properties are observed after each ignition operation and the sample evaluated accordingly. A Bunsen burner with a blue flame of natural gas 10 mm (⅜ inch) high with a heat content of $3.73 \times 10^4$ kJ/m$^3$ (1.000 BTU per cubic foot) is used to ignite the sample.

The UL 94 V 0 classification designates the properties, described below, of materials which have been tested in accordance with the UL 94 specification. The polycarbonates in this class contain no samples which burn for longer than 10 seconds after each action of the test flame; they show no overall flaming time greater than 50 seconds when the flame is allowed to act twice on each set of samples; they contain no samples which burn completely up to the top end of the sample, attached to the holding chamber; they contain no samples which ignite the wadding located beneath the sample as a result of burning drops or particles; they also contain no samples which glow for longer than 30 seconds after the test flame has been removed.

Other UL 94 classifications describe samples which are less flame-repellant and self-extinguishing and which release flaming drops or particles. These classifications are designated UL 94 V-1 and V-2. The polycarbonates within the range of this invention characteristically show the properties required for a UL 94 V 0 classification.

EXAMPLES

A. Preparation of a phthalimide of the general formula (I)

A1 N-(3,5-Bis-trifluoromethylphenyl)-phthalimide 800 ml of glacial acetic acid are initially introduced into a three-necked flask provided with a thermometer, stirrer and water separator, and are warmed to 55° C. A mixture of 44.4 g (0.3 mol) of phthalic anhydride and 68.7 g (0.3 mol) of distilled 3,5-bis-trifluoromethylaniline is then added and the components are stirred vigorously. On warming to 108° C., a clear solution is obtained. This is kept under reflux at 117° C. for 2½ hours and is then cooled. 100 ml of cyclohexane are added to the reaction mixture and the mixture is kept under reflux at 93° C. for 5 hours, during which the water of reaction can be removed in the water separator.

The glacial acetic acid is distilled off and the end product is boiled up in toluene, the mixture is filtered hot and the filtrate is cooled. The crystals which have precipitated are suspended in petroleum ether, filtered off with suction and dried.

% N theory: 3.91; % C theory: 53.6; % H theory: 1.96 %(N found: 3.85; % C found: 53.3; % H found: 1.84.

B. Flame-repellant, branched polycarbonate (comparison)

A branched polycarbonate based on bisphenol A, 0.5 mol % of 3,3-bis-(4-hydroxy-3-methylphenyl)-2-oxo-2,3-dihydroindole, 3.0 mol % of phenol, as a chain stopper, and phosgene and having a solution viscosity of 1.31 (measured in CH$_2$Cl$_2$ at 25° C. in a concentration of 0.5 g/100 ml) was mixed with 0.1% of K n-perfluorobutylsulphonate and the mixture was extruded and its fire-repellancy in a thickness of 3.2 mm and 1.6 mm was investigated according to UL 94.
Result:
3.2 mm V 0
1.6 mm V 2

C. Flame-repellant, branched polycarbonate according to the invention

A branched polycarbonate based on bisphenol A, 0.5 mol % of 3,3-bis-(4-hydroxy-3-methylphenyl)-2-oxo-2,3-dihydroindole, 3.0 mol % of phenol, as a chain stopper, and phosgene and having a solution viscosity of 1.31 (measured in CH$_2$Cl$_2$ at 25° C. in a concentration of 0.5 g/100 ml) were mixed with 0.1% of K n-perfluorobutanesulphonate and 0.5% of N-(3,5-bis-trifluoromethylphenyl)phthalimide according to Example A1, and the mixture was extruded and its fire-repellancy was investigated in a thickness of 3.2 mm, 1.6 mm and 0.8 mm in accordance with UL 94.
Result:
3.2 mm V 0
1.6 mm V 0
0.8 mm V 1

We claim:
1. A process for flameproofing thermoplastic, branched, aromatic polycarbonates made from halogen-free, phenolic components, comprising incorporating therein about 0.1 to 1% by weight, based on the polycarbonate, of a phthalimide of the formula

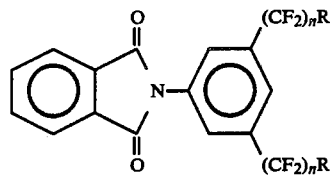

wherein
n is an integer from 1 to 12 and
R is hydrogen or a fluorine atom and 0.02 to 2% by weight based on the polycarbonate of an alkali metal salt of an organic or inorganic acid.
2. A process according to claim 1 wherein the phthalimide and the metal salt are incorporated individually or as a mixture, by mixing and subsequent granulation via a twin-screw extruder at a composition temperature of 280°–310° C., and a throughput of 5 kg/hour is achieved at a speed of rotation of 80–100 revolutions/minute.
3. A process according to claim 2 wherein the composition temperature is 290°–300° C.

* * * * *